United States Patent [19]
Torii et al.

[11] Patent Number: 5,929,233
[45] Date of Patent: *Jul. 27, 1999

[54] CYCLIZATION FOR PREPARING HALO-CEPHEMS

[75] Inventors: Sigeru Torii; Hideo Tanaka, both of Okayama-ken; Michio Sasaoka, Tokushima; Yutaka Kameyama, Tokushima; Isao Wada, Tokushima; Yasuhisa Amano, Tokushima, all of Japan

[73] Assignee: Otsuka Kagaku Kabushiki Kaisha, Osaka-Fu, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/732,445

[22] PCT Filed: Mar. 8, 1996

[86] PCT No.: PCT/JP96/00575

§ 371 Date: Nov. 6, 1996

§ 102(e) Date: Nov. 6, 1996

[87] PCT Pub. No.: WO96/29334

PCT Pub. Date: Sep. 26, 1996

[30] Foreign Application Priority Data

Mar. 10, 1995 [JP] Japan ................................ 7-079487
Mar. 10, 1995 [JP] Japan ................................ 7-079490

[51] Int. Cl.$^6$ .................... C07D 501/08; C07D 205/095
[52] U.S. Cl. ........................ 540/215; 540/221; 540/222; 540/358
[58] Field of Search ...................... 540/215, 221, 540/222

[56] References Cited

U.S. PATENT DOCUMENTS 5,162,524 11/1992 Farina ..................... 540/358
5,204,458 4/1993 Torii ....................... 540/215

FOREIGN PATENT DOCUMENTS 4-282387 10/1992 Japan .
616685 4/1980 Switzerland .

OTHER PUBLICATIONS

Tanaka et al, Nippon Kaga Kukai #61, Spring Annual Meeting 1991, Section C 9, #46, p. 1832, with Translation.
Tanaka, Syn Lett 1991, p. 888.
Kukolja, J. Org Chem 41, 2276 (1976).
Abstract for JP 4–282387 (1992).

Primary Examiner—Mark L. Berch
Attorney, Agent, or Firm—Nikaido Marmelstein Murray & Oram LLP

[57] ABSTRACT

The invention provides a process for preparing an allenyl β-lactam of formula (4), by reacting the hydroxyl group of a β-lactam of formula (1) with a reactive derivative of sulfonic acid of formula (2) to convert the compound of formula (1) to a β-lactam of formula (3), thereafter reacting the resulting β-lactam with a basic anion exchange resin of the type having a tertiary organic base fixed to the resin and isolating the allenyl β-lactam of formula (4) with stability and high purity in a high yield.

The invention also provides a process for preparing an allenyl β-lactam of formula (4), by reacting the hydroxyl group of a β-lactam compound of formula (1) with a reactive derivative of sulfonic acid of formula (2) to convert the compound of the formula (1) to a β-lactam compound of formula (3), thereafter reacting the resulting β-lactam of formula (3) with a tertiary organic base to convert the compound (3) to the allenyl β-lactam of formula (4), thereafter causing two kinds of ion exchange resins, i.e., an acidic cation exchange resin and a basic anion exchange resin, to alternately or simultaneously act on the lactam of formula (4) and isolating the allenyl β-lactam of formula (4).

Further, the invention provides a process for preparing a 3-halogenated cephem of formula (6), characterized by causing a halogenating reagent to act on an allenyl β-lactam of formula (4) in the presence of a sulfinate ion or thiolate ion capturing agent to obtain the 3-halogenated cephem.

9 Claims, No Drawings

CYCLIZATION FOR PREPARING HALO-CEPHEMS

(TECHNICAL FIELD)

The present invention relates to processes for preparing allenyl β-lactam compounds and 3-halogenated cephem derivatives.

The allenyl β-lactam compounds of the present invention are important intermediates for readily giving 3-substituted cephalosporins which are useful as starting materials, for example, for cefaclor, cefprozil or ceftibuten (S. Torni et al, Synlett., 1991, 888; J. Kanto et al, Tetrahedron Lett., 1992, 33, 3563; and S. Torii et al, Tetrahedron Lett., 1992, 33, 7029). The 3-halogenated cephem derivatives of the invention are also important intermediates for giving cephem antibiotics which are useful for oral administration (JP-A-39313/1986).

(BACKGROUND ART)

The allenyl β-lactam compound represented by the general formula (4) given below is conventionally prepared, for example, by reacting a tertiary organic base with the starting material in an organic solvent according to the process disclosed in JP-A-282359/1992. However, this compound is unstable when present in the resulting reaction mixture, which therefore usually requires cumbersome repeated procedures for extraction and concentration after the completion of the reaction. These procedures require time in the case of a large scale production, consequently entailing problems such as a marked reduction in the yield of the isolated product. Thus, processes still remain to be developed which are satisfactorily feasible for the preparation of allenyl β-lactam compounds.

Reports have been made on widely acceptable processes for preparing 3-halogenated cephem derivatives represented by the general formula (6) given below. These processes include a process which uses a compound of the general formula (7), i.e., 3-hydroxycephem compound, as the starting material and involves the conversion of hydroxyl group to trifluoromesyloxy group first and the subsequent reaction with a lithium halide as described in J. Org. Chem., 54, 4962(1989), a process wherein a reactive chlorine or bromine compound (such as phosphorus trichloride, phosphorus oxychloride or thionyl bromide) is reacted with a 3--hydroxycephem compound in dimethylformamide as disclosed in JP-A-116095/1974), and further a process wherein an alkali metal salt or alkaline-earth metal salt of a halogen is reacted with an allenyl β-lactam compound as disclosed in JP-A-282387/1992

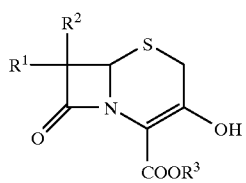

(7)

wherein $R^1$, $R^2$ and $R^3$ are as defined below.

The first of the processes requires the use of the 3-hydroxycephem compound as the starting material which compound itself is difficult to prepare, so that the process is in no way practically feasible. The second process inevitably forms 3-sulfonylcephem or 3-thiocephem as a by-product due to the recombination of sulfinate ion or thiolate ion which is released on ring closure, consequently giving the desired 3-halogenated cephem derivative in a yield of as low as up to 70%.

An object of the present invention is to provide a process wherein a β-lactam compound represented by the general formula (1) is used as the starting material for preparing an allenyl β-lactam compound of the general formula (4) as isolated with stability and high purity in a high yield by a simplified procedure.

Another object of the invention is to overcome the drawbacks of the conventional production processes described and to provide a widely-useful process for preparing the desired 3-halogenated cephem derivative in a high yield with a high purity.

(DISCLOSURE OF THE INVENTION)

The present invention provides a process for preparing an allenyl β-lactam compound represented by the general formula (4), characterized by reacting the hydroxyl group of a β-lactam compound represented by the general formula (1) with a reactive functional group derivative of sulfonic acid represented by the general formula (2) to convert the compound of the formula (1) to a β-lactam compound represented by the general formula (3), thereafter reacting the resulting β-lactam compound with a basic anion exchange resin of the type having a tertiary organic base fixed to the resin and isolating the allenyl β-lactam compound of the formula (4) from the reaction mixture with stability and high purity in a high yield

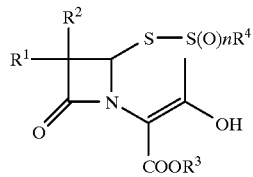

(1)

wherein $R^1$ is a hydrogen atom, amino or protected amino, $R^2$ is a hydrogen atom, halogen atom, lower alkoxyl, lower acyl, or lower alkyl having hydroxyl or protected hydroxyl as a substituent, $R^3$ is a hydrogen atom or carboxylic acid protecting group, $R^4$ is an aromatic compound residue which may have a substituent or nitrogen-containing aromatic heterocyclic compound residue which may have a substituent, and n is 0 to 2

$$R^5\text{—SO}_2\text{—X} \tag{2}$$

wherein $R^5$ is an aliphatic, alicyclic or aromatic hydrocarbon group which may have a substituent, and X is a halogen atom or $OSO_2R^5$ group

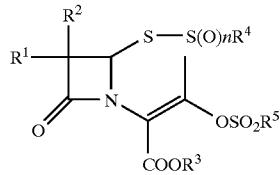

(3)

wherein $R^1$, $R^2$, $R^3$, $R^4$, $R^5$ and n are as defined above

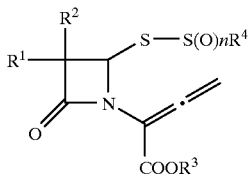

(4)

wherein $R^1$, $R^2$, $R^3$, $R^4$ and n are as defined above.

The present invention also provides a process for preparing an allenyl β-lactam compound represented by the general formula (4), characterized by reacting a β-lactam compound represented by the general formula (3) with a tertiary organic base conventionally used to convert the compound (3) to the allenyl β-lactam compound of the formula (4), thereafter causing two kinds of ion exchange resins, i.e., an acidic cation exchange resin and a basic anion exchange resin, to alternately or simultaneously act on the β-lactam compound of the formula (4) and isolating the allenyl β-lactam compound of the formula (4) from the resulting reaction solution with stability and high purity in a high yield.

In solving the problems of the foregoing known processes while developing processes for preparing allenyl β-lactam compounds, we found that the decomposition of the allenyl β-lactam compound is attributable to the presence of a very small excess of the tertiary organic base or a salt of the tertiary organic base and sulfonic acid remaining after the completion of the allenization reaction. This finding has led us to the discovery of the entirely novel fact that when a basic ion exchange resin of the type which has a tertiary organic base fixed to the resin and which is used in place of the tertiary organic base is caused to act on the β-lactam compound of the formula (3), the allenyl β-lactam compound of the formula (4) which was conventionally unstable can be isolated from the resulting reaction mixture by a usual procedure with stability and high purity in a high yield.

We have further found the entirely novel fact that the allenyl β-lactam compound represented by the general formula (4) can be prepared with stability and high purity in a high yield from a reaction mixture through a usual isolation procedure, by reacting a β-lactam compound represented by the general formula (3) with a tertiary organic base as practiced conventionally, and thereafter removing the tertiary organic base or a tertiary organic base component which is the salt of the organic base and sulfonic acid from the reaction mixture with an acidic cation exchange resin and removing the sulfonic acid of the salt of the base and the acid from the reaction mixture with a basic anion exchange resin, or repeating these procedures with use of the same resin or the different resins, whereby the present invention has been accomplished.

The present invention further provides a process for preparing a 3-halogenated cephem derivative represented by the general formula (6), characterized by causing a halogenating reagent to act on an allenyl β-lactam compound represented by the general formula (4) in the presence of a sulfinate ion or thiolate ion capturing agent to obtain the 3-halogenated cephem derivative

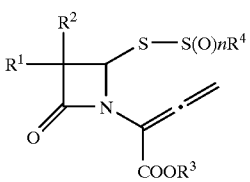

(4)

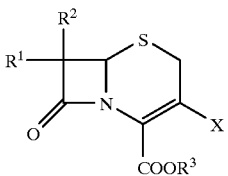

(6)

wherein $R^1$, $R^2$, $R^3$, $R^4$ and n are as defined above, X is a halogen atom.

In providing a widely useful process for preparing 3-halogenated cephem derivatives, we directed attention to the process disclosed in the aforementioned publication JP-A-282387/1992 wherein an alkali metal halide or alkaline earth metal halide is caused to act on an allenyl β-lactam compound. The process of JP-A-282387/1992 inevitably involves the formation of 3-sulfonylcephem or 3-thiocephem as a by-product due to the recombination of sulfinate ion or thiolate ion which is released on ring closure, consequently affording the desired 3-halogenated cephem derivative in a yield of up to 70%.

Accordingly, we made an intensive investigation on various additives that would react with sulfinate ion, thiolate ion or like released group for inactivation and found that the released sulfinate ion or thiolate ion can be captured by adding to the reaction system a silylating agent, acid halide, acid anhydride, sulfonyl halide, sulfonic anhydride or aluminum halide. This finding has led us to the discovery of the entirely novel fact that use of such a capturing agent and a halogenating reagent in combination quantitatively affords the desired 3-halogenated cephem derivative.

We have also recognized the novel fact that silyl halides and aluminum halides not only act as capturing agents but also function as halogenating agents.

Examples of groups mentioned herein are as follows.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenyllacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc. imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218–287). Examples of protective groups for the amino of phenylglycylamido group and p-hydroxyphenylglycylamido group are those disclosed in the literature, Chap. 7 (pp. 218–287). Examples of protective groups for the hydroxyl of p-hydroxyphenylglycylamido group are those disclosed in the literature, Chap.2 (pp. 10–72).

Further, also are included groups of the formula (A)

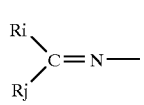

(A)

wherein Ri and Rj are same or different and each a hydrogen atom, aliphatic or aromatic hydrocarbon group or heterocyclic hydrocarbon group, or may bond together to form a cyclic group.

Examples of halogen atom represented by $R^2$ are fluorine, chlorine, bromine or iodine atom. Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with hydroxyl or protected hydroxyl, and for the protected hydroxyl represented by $R^2$ are those disclosed in the literature, Chap. 2 (pp. 10–72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl. Examples of lower alkyl are straight-chain or branched $C_{1-4}$ alkyl group such as methyl, ethyl, n-propyl, isopropyl, n-butyl, isobutyl, sec-butyl or tert-butyl.

Exemplary of the carboxylic acid protecting group represented by $R^5$ are allyl, benzyl, p-methoxybenzyl, p-nitrobenzyl, diphenylmethyl, trichloromethyl, tert-butyl, and those disclosed in the literature, Chap. 5 (pp. 152–192).

Examples of aromatic residue, substituted aromatic residue, nitrogen-containing aromatic residue and substituted nitrogen-containing aromatic residue represented by $R^4$ are phenyl, naphthyl, benzothiazol, triazol, thiazol, tetrazol group, etc. Exemplary of the substituent which may be substituted in these groups are halogen atoms (such as fluorine, chlorine, bromine, iodine atom), straight-chain or branched $C_{1-4}$ alkoxyl groups (such as methoxy, ethoxy), straight-chain or branched $C_{1-4}$ alkylthio groups (such as methylthio, ethylthio), straight-chain or branched $C_{1-4}$ alkyl-sulfonyloxy groups (such as methanesulfonyloxy, trifluoromethanesulfonyl-oxy), aromatic sulfonyloxy or substituted aromatic sulfonyloxy (such as benzenesulfonyloxy, toluenesulfonyloxy), straight-chain or branched $C_{1-4}$ alkyl groups (such as methyl, ethyl), amino, amino which has as a substituent one or two straight-chain or branched $C_{1-4}$ alkyl groups (such as methylamino, dimethylamino, ethylamino, diethylamino), hydroxyl, acyloxy group represented by R'COO— wherein R' is phenyl, tolyl, or straight-chain or branched $C_{1-4}$ alkyl group (such as phenylcarbonyloxy, acetyloxy), acyl group represented by R'CO— wherein R' is as defined above (such as phenylcarbonyl, acetyl), nitro, cyano, phenyl, etc. When the aryl represented by Ar is phenyl group, the aryl may have 1 to 5, especially 1, 2 or 3, same or different groups selected from among the above substituents. When the aryl represented by Ar is naphtyl group, the aryl may have 1 to 7, especially 1, 2 or 3, same or different groups selected from among the above substituents.

Examples of aliphatic, alicyclic or aromatic hydrocarbon groups which may have a substituent represented by $R^5$ are straight-chain or branched $C_{1-4}$ alkyl groups (such as methyl, ethyl), alkenyl groups (such as allyl, butenyl) and like aliphatic hydrocarbon groups, $C_{3-8}$ cycloalkyl groups (such as cyclopentyl, cyclohexyl) and like alicyclic hydrocarbon groups, phenyl, naphthyl and like aromatic hydrocarbon groups. Exemplary of the substituent which may be substituted in these hydrocarbon groups are halogen atoms (such as fluorine, chlorine, bromine, iodine atom), straight-chain or branched $C_{1-4}$ alkoxyl groups (such as methoxy, ethoxy), straight-chain or branched $C_{1-4}$ alkylthio groups (such as methylthio, ethylthio), straight-chain or branched $C_{1-4}$ alkyl groups (such as methyl, ethyl), amino, amino which has as a substituent one or two straight-chain or branched $C_{1-4}$ alkyl groups (such as methylamino, diethylamino), hydroxyl, acyloxy group represented by R'COO— wherein R' is phenyl, tolyl, or straight-chain or branched $C_{1-4}$ alkyl group (such as phenylcarbonyloxy, acetyloxy), acyl group represented by R'CO— wherein R' is as defined above (such as phenylcarbonyl, acetyl), nitro, cyano, phenyl, etc. The hydrocarbon groups represented by $R^5$ may have 1 to 5, especially 1 to 3, same or different groups selected from among the above substituents. $R^5$ is preferably methyl, ethyl, trifluoromethyl, tolyl and phenyl.

Examples of tertiary organic bases for use in the allenization reaction are those wherein the three substituents are each an aliphatic, alicyclic or aromatic hydrocarbon group which may have a substituent. The three hydrocarbon groups can be the same or different, while two of these groups may be combined together to form a ring through a carbon—carbon bond, oxygen-carbon bond, sulfur-carbon bond, nitrogen-carbon bond or lower alkyl substituting nitrogen-carbon bond. Examples of suitable tertiary organic bases are $C_1$ to $C_4$ straight-chain or branched-chain trialkylamines such as diethylmethylamine, diisopropylethylamine, diisopropylmethylamine, tributylamine and diisobutylmethylamine, $C_3$ to $C_8$ dicycloalkylalkylamines such as dicyclopropylmethylamine, dicyclopentylmethylamine and dicyclohexylmethylamine, $C_3$ to $C_8$ tricycloalkylamines such as tricyclopropylamine, tricyclopentylamine and tricyclohexylamine, and others including N-methylaziridine, N-methylpyrrolidine, N-methylpiperidine, N-methyhexahydroazepin, N-methylmorpholine, N-methylthiomorpholine, N,N-dimethylpiperazine and 4-methyl-1-piperazine. Examples of substituents for use in the three hydrocarbon groups are the same as those exemplified for use in the aliphatic, alicycle or aromatic hydrocarbon group represented by $R^3$ and having up to 18 carbon atoms. The hydrocarbon group may be substituted with 1 to 5, preferably 1 to 3, such substituents, which are the same or different.

The β-lactam compound represented by the formula (1) and serving as a starting material of the invention can be prepared, for example, by the following process. β-lactam compound represented by the general formula (5) is reacted with ozone in an inert solvent at a low temperature and then reduced with a reducing agent such as dimethyl sulfide, whereby the desired compound can be obtained

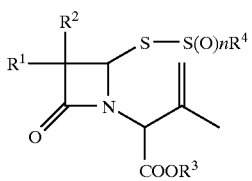

(5)

wherein $R^1$, $R^2$, $R^3$, $R^4$ and n are as defined above.

The ozonolysis reaction can be carried out under the conditions described in "Shin Jikken Kagaku Koza," edited by Nihon Kagakukai, Vol. 15, 593–603.

The reaction is conducted in a suitable solvent. Examples of solvents useful in the above reaction are alcohols such as methanol, ethanol, propanol, isopropanol, butanol and tert-butanol, lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran and dioxane, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfexide, etc. These solvents are used singly or in admixture of at least two of them. These solvents may contain water as required.

These solvents are used in an amount of about 10 to about 200 liters, preferably about 20 to about 100 liters, per kilogram of the compound of the formula (5). The reaction is conducted usually at −78° C. to 0° C., preferably −60° C. to −25 ° C.

The amount of ozone to be used for the reaction is usually one equivalent relative to the starting compound (5), whereas the ozone may be passed through the reaction system until the starting compound (5) no longer remains when so required. When the amount of ozone is in excess of one equivalent, it is desired to pass dry nitrogen through the reaction mixture to drive off an excess of ozone, followed by an aftertreatment.

The peroxides, such as ozonide, resulting from the reaction are reductively cleaved with a reducing agent for use in usual organic reactions, whereby the desired compound of the formula (1) is prepared. Examples of useful reducing agents are catalytic hydrogenating agents such as platinum, palladium, nickel and rhodium serving as catalysts, trivalent phosphorus compounds such as esters of phosphorous acid and triphenylphosphine, and sulfide compounds such as dimethyl sulfide and thiodiethanol. The compound of the formula (1) can be keto-enol tautomeric.

The hydroxyl group of the β-lactam compound represented by the formula (1) and thus obtained is reacted with a reactive functional group derivative of sulfonic acid represented by the general formula (2), $R^5$—$SO_2$—X wherein: $R^5$ and X are as defined above, whereby the compound can be converted to a β-lactam compound represented by the general formula (3).

Examples of reactive functional group derivatives of sulfonic acid of the formula (2), i.e., $R^5$—$SO_2$—X wherein $R^5$ and X are as defined above, to be used are reactive anhydrides thereof (e.g., lower unsubstituted or substituted alkylsulfonic anhydrides such as methanesulfonic anhydride, ethanesulfonic anhydride and trifluoromethanesulfonic anhydride) and mixed anhydrides of sulfonic acid and hydrohalogenic acids (e.g., lower alkylsulfonyl halides such as methanesulfonyl chloride, methanesulfonyl bromide, p-toluenesulfonyl chloride and p-toluenesulfonyl bromide). The amount of the reactive functional group derivative of sulfonic acid of the formula (2), $R^5$—$SO_2$—X wherein $R^5$ and X are as defined above, to be used for the reaction is usually 1 to 10 equivalents relative to the β-lactam compound of the formula (3), whereas the derivative may be used additionally until the β-lactam compound of the formula (3) disappears when so required.

The reaction of the compound (1) and the compound (2) is preferably conducted in the presence of a base. As the base are preferably used aliphatic or aromatic amine and carbonate of alkali metal or alkaline earth metal. Examples of bases are organic bases such as triethylamine, diisopropylamine, ethyldiisopropylamine, tributylamine, 1,5-diazabicyclo[4.4.0]nonene-5 (DBN), 1,8-diazabicyclo[5.4.0]-undecene-7 (DBU), 1,4-diazabicyclo[2.2.2]octane (Dabco), N-methylpiperidine, 2,2,6,6-tetramethylpiperidine, N-methyl-morpholine, N,N-dimethylaniline and N,N-dimethylaminopyridine, inorganic bases such-as sodium hydrogencarbonate, sodium carbonate, potassium hydrogencarbonate, potassium carbonate, lithium hydrogencarbonate and lithium carbonate. These bases are used usually in an amount of 1 to 10 equivalents based on the β-lactam compound of the formula (1). When required, it is recommended the base is added until the β-lactam compound of the formula (1) is consumed.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran and dioxane, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the compound of the formula (1).

The reaction is conducted usually at −78° C. to 50° C., preferably −40° C. to 0° C. The reaction can be conducted, as required, in a sealed vessel, or at an atmosphere of an inert gas such as nitrogen gas. The reaction proceeds promptly even at a low temperature, and sometimes affords a desired product at a high yield within ten minutes to one hour. The resulting β-lactam compound can be isolated by the usual extraction procedure but can be used in the next reaction in the form of the reaction mixture without purification.

The β-lactam compound of the formula (3) is treated with a basic anion exchange resin of the type having a tertiary organic base fixed to the resin, whereby the compound can be converted to an allenyl β-lactam compound represented by the formula (4). For the reaction, the basic anion exchange resin of the type mentioned is used usually in an amount of 1 to 10 equivalents relative to the β-lactam compound of the formula (3). When required, the resin is used additionally until no β-lactam compound of the formula (3) remains.

In the case where the β-lactam compound of the formula. (3) is reacted with a tertiary organic base to prepare the allenyl β-lactam compound of the formula (4) in the conventional manner, two kinds of ion exchange resins, i.e., an acidic cation exchange resin and a basic anion exchange resin, are cause to alternately or simultaneously act on the reaction mixture. This makes it possible to handle the resulting allenyl β-lactam compound with stability without permitting decomposition of the product.

The reaction for the conversion of the compound (3) to the compound (4) is conducted in a suitable solvent. Examples of solvents usable are those for use in the reaction for preparing the compound (3) from the compound (1). These solvents are used singly or in the form of a mixture of at least two of them. The solvent is used usually in an amount of about 1 to about 200 liters, preferably about 20 to about 100 liters, per kilogram of the compound of the formula (3).

In treating the compound (3) with the basic anion exchange resin of the type having a tertiary organic base fixed to the resin for conversion to the compound (4), the reaction is conducted usually in the temperature range of −30 to 80° C., preferably −10 to 40° C., although the temperature is variable with the kind of group —O—SO$_2$— R$^5$ and with the kind of amine to be used. The reaction is carried out in a closed container and/or in an inert gas such as nitrogen gas when so required. The reaction time generally varies with the reaction temperature, the concentration of the reaction system, the amount of reagent, etc., and is usually 0.1 hour to 20 hours, whereby the desired product can be obtained in a high yield. The allenyl β-lactam compound of the formula (4) can be isolated by a usual extraction procedure, or is alternatively usable as contained in the resulting reaction mixture for the subsequent reaction.

Examples of basic anion exchange resins usable in the reaction from the compound (3) to the compound (4) are Amberlite IRA-35, IRA-45, IRA-47, IRA-60E, IRA-68, IRA-93, IRA-93ZU, IRA-94, IRA-94S, IRA-400, IRA-400T, IRA-401, IRA-402, IRA-402BL, IRA-410, IRA-411, IRA-411S, IRA-430, IRA-440B, IRA-458, IRA-478, IRA-743T, IRA-900, IRA-904, IRA-910, IRA-911, IRA-938, IRA-958, XE-583, XT-5007, XT-5010, XT-5021, XT-5028, Amberlist A-26, A-27, A-21, Powdex PAO (Organo Co., Ltd.), basic anion exchange resin DOWEX (Dow Chemicals Co., Ltd.) and basic anion exchange resin DIAION (Mitsubishi Kasei Co., Ltd.).

The amount of the basic anion exchange resin to be used for the reaction is usually I to 20 equivalents, preferably 1 to 10 equivalents, relative to the β-lactam compound of the formula (3). When required, the basic anion exchange resin may be used additionally until the β-lactam compound of the formula (3) no longer remains.

The allenyl β-lactam compound of the formula (4) obtained can be isolated from the reaction mixture with stability through usual extraction and concentration procedures, but is usable for the subsequent reaction as separated by filtration from the resin used and as contained in the same reaction mixture.

When the conventional reaction for the-conversion of the compound (3) to the compound (4) with use of a tertiary organic base is followed by the treatment with two kinds of ion exchange resins, i.e., acidic cation exchange resin and basic anion exchange resin, which are used alternately or at the same time to remove the by-product, i.e., sulfonic acid or the salt of the tertiary organic base and sulfonic acid, from the reaction mixture, the basic anion exchange resin to be used for the aftertreatment can be the above-mentioned basic anion exchange resin. Examples of acidic cation exchange resins are Amberlite 200C, 201B, 252, IR-116, IR-118, IR-120B, IR-122, IR-124, IRC-50, IRC-76, IRC-84, IRC-718, XT-1004, XT-1006, XT-1007, XT-1016, Amberlist 15E, A-15E, Powdex PCH, PCN (Organo Co., Ltd), acidic cation exchange resin DOWEX (Dow Chemicals Co., Ltd.) and acidic cation exchange resin DIAION (Mitsubishi Kasei Co., Ltd.). The amount of basic anion exchange resin to be used for the reaction is usually 1 to 20 equivalents, preferably 1 to 10 equivalents, relative to the by-product, i.e., sulfonic acid or the salt of the tertiary organic base and the sulfonic acid, whereas the resin may be used additionally until the by-product no longer remains when so required. The amount of acidic cation exchange resin to be used for the reaction is usually 1 to 20 equivalents, preferably 1 to 10 equivalents, relative to the tertiary organic base used. When required, the resin may be used additionally until no base remains.

The treatment by the alternate or simultaneous use of the two kinds of ion exchange resins, i.e., acidic cation exchange resin and basic anion exchange resin, for removing the by-product of sulfonic acid or the salt thereof form the reaction mixture is carried usually in the range of −70 to 80° C., preferably −40 to 40° C., although the reaction rapidly proceeds generally at low temperatures. The treating time, which generally varies with the treatment temperature and concentration, the amount of resins, etc., is usually 0.1 hour to 20 hours. The allenyl β-lactam compound of the formula (4) obtained can be isolated from the reaction mixture with stability by usual extraction and concentration procedures, but is usable for the subsequent reaction as separated by filtration from the resins used and as contained in the same reaction mixture.

The allenyl β-lactam compound of the formula (4) serving as the starting material for the 3-halogenated cephem derivative of the invention can alternatively be prepared, for example, by the process disclosed in JP-A-282359/1992.

More specifically stated, the desired compound can be obtained by causing a base to act on a β-lactam compound represented by the general formula (3A) in an inert solvent.

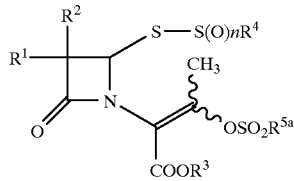

(3A)

wherein R$^1$, R$^2$, R$^3$, R$^4$ and n are as defined above, R$^5$ is lower alkyl, substituted lower alkyl, aryl or substituted aryl.

The reaction is conducted in a suitable solvent. Examples of solvents are those useful in the reaction from the compound.(5) to the compound (1). These solvents are used singly or in admixture of at least two of them. These solvents may contain water as required. These solvents are used in an amount of about 10 to about 200 liters, preferably about 20 to about 100 liters, per kilogram of the compound of the formula (3A) . The reaction is conducted usually at −78° C. to 60° C., preferably −40° C. to 30° C . Examples of useful bases are N,N,N-tri lower alkyl amines such as trimethylamine, dimethylethylamine, triethylamine and diisopropylethylamine, N-lower alkyl azacycloalkanes such as N-methylpiperidine and N-ethylpiperidine, N-phenyl lower alkyl-N,N-di lower alkyl amines such as N-benzyl-N,N-dimethylamine and N-benzyl-N,N-diethylamine, N,N-dialkyl aromatic amines such as N,N-dimethylaniline, nitrogen-containing aromatic amines such as pyridine, bicycloamines such as diazabicycloundecene and diazabicyclononene, and a mixture of these amines. These bases are used usually in an amount of 1 to 10 equivalents based on the β-lactam compound of the formula (3A). When required, it is recommended the base is added until the 6 -lactam compound of the formula (3A) is consumed. The resulting allenyl β-lactam compound of the formula (4) can be isolated by the usual purification method but can be used in the next reaction without purification.

The allenyl β-lactam compound represented by the formula (4) can be converted to a 3-halogenated cephem derivative represented by the general formula (6) by causing a halogenating reagent to act on the allenyl group of the β-lactam compound (4) in an inert solvent in the presence of a sulfinate ion or thiolate ion capturing agent such as a silylating agent, acid halide, acid anhydride, sulfonyl halide, sulfonic anhydride or aluminum halide. A silyl halide derivative or aluminum halide, if used for this reaction, is serviceable as both the sulfinate ion or thiolate ion capturing agent and the halogenating agent.

Examples of useful silylating agents are trimethylsilyl chloride, O,N-bistrimethylsilylacetamide, bistrimethylsilylurea, hexamethyldisilazane, hexamethyldisilane, etc., among which O,N-bistrimethylsilylacetamide and bistrimethylsilylurea are preferred.

Examples of useful aluminum halides are aluminum fluoride, aluminum chloride, aluminum bromide and aluminum iodide, among which aluminum chloride and aluminum bromide are desirable.

Examples of useful acid halides are acetyl chloride, chloroacetyl chloride, acetoxyacetyl chloride, acetoacetyl chloride, acetyl bromide, formyl chloride, propanoyl chloride, butanoyl chloride and like lower alkyl acid halides which may have a substituent, methyl chlorocarbonate, ethyl chlorocarbonate, isopropyl chlorocarbonate, butyl chlorocarbonate and like lower alkyl carbonic acid halides, oxalyl chloride, tartaryl dichloride, succinyl dichloride, malonyl dichloride and like diacid halides, etc. Examples of useful acid anhydrides are acetic anhydride, trifluoroacetic anhydride, succinic anhydride, malonic anhydride and like lower alkyl acid anhydrides. Examples of useful sulfonyl halides are methanesulfonyl chloride, ethanesulfonyl chloride, benzylsulfonyl chloride and lower alkylsulfonyl chlorides which may have a substituent, benzenesulfonyl chloride, toluenesulfonyl chloride and like arylsulfonyl chlorides which may have a substituent, and fluorosulfonyl chloride and like halogenosulfonyl chlorides. Examples of useful sulfonic anhydrides are methanesulfonic anhydride, trifluoromethanesulfonic anhydride and like lower alkylsulfonic anhydrides which may have a substituent, benzenesulfonic anhydride, toluenesulfonic anhydride and like arylsulfonic anhydrides which may have a substituent, and fluorosulfonic anhydride and like halogenosulfonic anhydrides. These acid halides, acid anhydrides, sulfonyl halides and sulfonic anhydrides may be used singly or in the form of a mixture of at least two of them.

Examples of halogenating reagents which are used conjointly with the ion capturing agent are metal halides and quaternary ammonium halides. Examples of metal halides usable are aluminum chloride, aluminum bromide and like aluminum halides, silyl halide derivatives of which trimethylsilyl chloride is typical, and various metal salts. Among these, halogen salts of alkali metals and alkaline-earth metals are preferred. Examples of such salts are lithium chloride, lithium bromide, lithium iodide, calcium chloride, calcium bromide, calcium iodide, barium chloride, barium bromide, barium iodide, strontium chloride, strontium bromide, strontium iodide, etc. Examples of useful quaternary ammonium halides are ammonium chloride, triethylamine hydrochloride, tetra-n-butylammonium chloride, triethylbenzylammonium bromide, tetrabenzylammonium, halide etc. Aluminum halides and halogenating reagents are used in an amount of 1 to 30 equivalents, preferably 1 to 10 equivalents, relative to the allenyl β-lactam compound represented by the formula (4). When required, the agent and reagent may be additionaly used until the allenyl β-lactam compound of the formula (4) disappears.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclboctane, amides such as dimethylformamide, dimethylacetamide and N-methyl-2-pyrrolidone or cyclic amide, dimethylsulfoxide, etc. These solvents are used singly or in admixture of at least two of them. These solvents are used in an amount of about 10 to about 200 liters, preferably about 20 to about 100 liters, per kilogram of the compound of the formula (4). The reaction is conducted usually at −78 ° C. to 60° C., preferably −20° C. to 30° C. The reaction can be conducted, as required, in a sealed vessel, or at an atmosphere of an inert gas such as nitrogen gas. The resulting 3-halogenated cephem derivative can be isolated by the usual purification methods.

(BEST MODE OF CARRYING OUT THE INVENTION)

The present invention will be clarified in greater detail with reference to the following examples but is not limited to the examples. Ph stands for $C_6H_5$—.

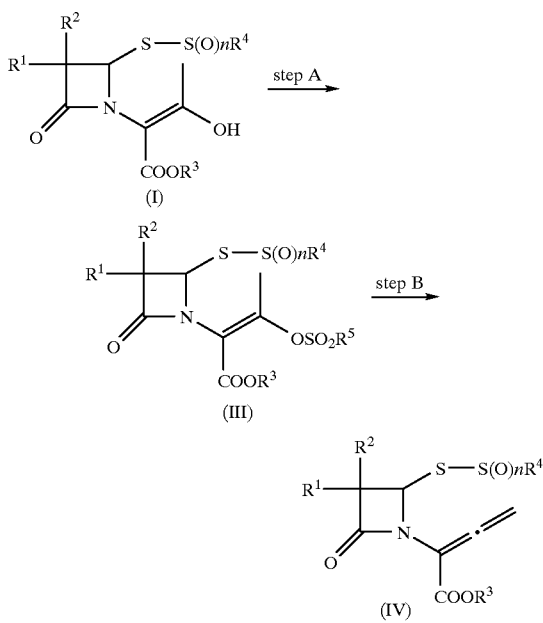

EXAMPLE 1

(Preparation of Material)

A 100.0 g quantity of compound (5a) ($R^1$=PhCH$_2$CONH, $R^2$=H, $R^3$=p-MeOC$_6$H$_4$CH$_2$, $R^4$=Ph, n=2) was dissolved in 500 ml of ethyl acetate; followed by cooling to −70° C. Ozone (O$_3$, 22.1 mmoles/hr) was passed through the solution, and 5 hours and 20 minutes later, complete disappearance of compound (5a) was confirmed by liquid chromatography, whereupon 36 ml of dimethyl sulfide was added to the reaction mixture. The resulting mixture was slowly heated to 25° C. After 16 hours, the reaction mixture was washed with 500 ml of water twice, and the ethyl acetate layer was dried over magnesium sulfate and thereafter concentrated in vacuo to remove the solvent and obtain a residue containing compound (1a) ($R^1$=PhCH$_2$CONH, $R^2$=H, $R^3$=p-MeOC6H$_4$CH$_2$, $R^4$=Ph, n=2). The residue was crystallized with 500 ml of 50% aqueous isopropyl alcohol, giving 95.3 g (yield 95% ) of compound (1a).

(Step A)

A 30.0 g quantity of compound (1a) ($R^1$=PhCH$_2$CONH, $R^2$=H, $R^3$=p-MeOC$_6$H$_4$CH$_2$, $R^4$=Ph, n=2) was dissolved in 300 ml of dimethylformamide dried with a molecular sieve 4 Å, and the solution was cooled to 3° C. To the solution were added 10.4 g of p-toluenesulfonyl chloride first and then 11.9 g of Na$_2$CO$_3$ at the same temperature. Complete disappearance of compound (1a) was confirmed by liquid chromatography 1 hour later, 2000 ml of ethyl acetate was thereafter added to the reaction mixture, and the ethyl acetate layer was washed with water once, with aq. 1N HCl once, with aq. 10% NaHCO$_3$ once and with 10% aqueous NaCl solution once. The ethyl acetate layer was dried over magnesium sulfate and then concentrated in vacuo to remove the solvent and obtain a residue containing compound (3a-1) ($R^1$=PhCH$_2$CONH, $R^2$=H, $R_3$=p-MeOC$_6$H$_4$CH$_2$ , $R^4$=Ph, n=2, $R^5$=C$_6$H$_4$CH$_3$). The residue was purified by silica gel chromatography (benzene/ethyl acetate=5/1), giving 38.1 g (yield 95% ) of compound (3a-1).

(Step B)

A 1.0 g quantity of compound (3a-1) ($R^1$=PhCH$_2$CONH, $R^2$=H, $R^3$=p-MeOC$_6$H$_4$CH$_2$, $R^4$=Ph, n=2, $R^5$ =Co H$_4$CHS) was dissolved in 10 ml of dimethylformamide dried with a molecular sieve 4 Å and 1.4 g of basic anion exchange resin (XE-583) was placed into the solution at 25° C. Disappearance of compound (3a-1) was confirmed by liquid chromatography 5 hours later, 100 ml of ethyl acetate was thereafter added to the reaction mixture, and the ethyl acetate layer was washed with water once, with aq. 1 N HCl once, with aq. 10% NaHCO$_3$ once and with 10% aqueous NaCl solution once. The ethyl acetate layer was dried over magnesium sulfate, followed by the removal of the solvent in a vacuum to obtain a residue containing compound (4a) ($R^1$=PhCH$_2$CONH, $R^2$=H, $R^3$=p-MeOCeH$_4$CH$_2$, $R^4$=Ph, n=2). The residue was purified by silica gel chromatography (benzene/ethyl acetate=4/1 to 1/1), giving 0.68 g (yield 93% ) of compound (4a).

$^1$H NMR(30 OMHz, CDCl$_3$)δ: 3.60(s, 2H), 3.80(s, 3H), 5.10(s, 2H), 5.33(dd, J=5.0, 8.3 Hz, 1H), 5.48, 5.62(ABq, J=15.3 Hz, 2H), 5.87(d, J=5.OHz, 1H), 6.05(d, J=8.3Hz, 1H), 6.85–7.85(m, 14H)

EXAMPLE 2

(Preparation of Material)

A 100.0 g quantity of compound (5b) ($R^1$=PhCH$_2$CONH, $R^2$=H, RS=CHPh$_2$, $R^4$=Ph, n=2) was dissolved in 500 ml of ethyl acetate, followed by cooling to −70° C. Ozone (03, 22.1 mmoles/hr) was passed through the solution, and 5 hours and 20 minutes later, complete disappearance of compound (5b) was confirmed by liquid chromatography, whereupon 33.5 ml of dimethyl sulfide was added to the reaction mixture. The resulting mixture was slowly heated to 25° C . After 16 hours, the reaction mixture was washed with 500 ml of water twice, and the ethyl acetate layer was dried over magnesium sulfate and thereafter concentrated in vacuo to remove the solvent and obtain a residue containing compound (1b) ($R^1$=PhCH$_2$CONH, $R^2$=H, $R^3$=CHPh$_2$, $R^4$=Ph, n=2). The residue was crystallized with 500 ml of 50% aqueous isopropyl alcohol, affording 95.3 g (yield 95% ) of compound (1b).

(Step A)

A 30.0 g quantity of compound (1b) ($R^1$=PhCH$_2$CONH, $R^2$=H, $R^3$=CHPh$_2$, $R^4$=Ph, n=2) was dissolved in 300 ml of dimethylformamide dried with a molecular sieve 4 Å, and the solution was cooled to 3° C. To the solution were added 10.7 g of p-toluenesulfonyl chloride first and then 11.9 g of Na$_2$CO$_3$ at the same temperature. Complete disappearance of compound (1b) was confirmed by liquid chromatography 1 hour later, 2000 ml of ethyl acetate was thereafter added to the reaction mixture, and the ethyl acetate layer was washed with water once, with aq. 1N HCl once, with aq. 10% NaHCO$_3$ once and with 10% aqueous NaCl solution once. The ethyl acetate layer was dried over magnesium sulfate and then concentrated in vacuo to remove the solvent and obtain a residue containing compound (3b-1) ($R^1$=PhCH$_2$CONH, $R^2$=H, $R^3$=CHPh$_2$, $R^4$=Ph, n=2, $R^5$=C$_6$H$_4$ CH$_3$)

The residue was purified by silica gel chromatography (benzene/ethyl acetate=5/1), giving 38.4 g (yield 95% ) of compound (3b-1).

(Step B)

A 1.0 g quantity of compound (3-1) ($R^1$=PhCH$_2$CONH, $R^2$=H, $R^3$=CHPh$_2$, $R^4$=Ph, n=2, $R^5$=C$_6$H$_4$CH$_5$) was dissolved in 10 ml of dimethylformamide dried with a molecular sieve 4Å, and 1.4 g of weakly basic anion exchange resin (XE-583) was placed into the solution at 25° C. Disappearance of compound (3b-1) was confirmed by liquid chromatography 5 hours later, 100 ml of ethyl acetate was thereafter added to the reaction mixture, and the ethyl acetate layer was washed with water once, with aq. 1N HCl once, with aq. 10% $NaHCO_3$ once and with 10% aqueous NaCl solution once. The ethyl acetate layer was dried over magnesium sulfate, followed by the removal of the solvent in vacuo to obtain a residue containing compound (4b) ($R^1$=$PhCH_2CONH$, $R^2$=H, $R^3$=$CHPh_2$, $R^4$=Ph, n=2). The residue was purified by silica gel chromatography (benzene/ethyl acetate=4/1 to 1/1), giving 0.68 g (yield 92%) of compound (4b).

$^1$H NMR(300 MHz, $CDCl_{32}$)δ:3.61(s, 2H), 5.31(dd, J=4.4, 8.0 Hz, 1H), 5.57, 5.70(ABq, J=15.2 Hz, 2H), 5.84(d, J=4.4 Hz, 1H), 6.02(d, J=8.0 Hz, 1H), 6.81(s, 1H), 7.22–7.73(m, 20H)

EXAMPLE 3

(Step A)

A 10.0 g quantity of compound (1b) ($R^1$=$PhCH_2CONH$, $R^2$=H, $R^3$=$CHPh_2$, $R^4$=Ph, n=2) was dissolved in 100 ml of methylene dichloride dried with a molecular sieve 4 Å, and the solution was cooled to −20° C. A 1.8 ml quantity of methanesulfonyl chloride was added to the solution, and 3.5 ml of tritethylamine was thereafter added dropwise to the solution at the same temperature over a period of 15 minutes. Complete disappearance of compound (1b) was confirmed by liquid chromatography 30 minutes later, and the methylene dichloride layer was thereafter washed with water once, with aq. 1 N HCl once, with aq. 10% $NaHCO_3$ once and with 10% aqueous NaCl solution once. The methylene dichloride layer was dried over magnesium chloride, followed by the removal of the solvent in vacuo to obtain a residue containing compound (3b-2) ($R^1$=$PhCH_2CONH$, $R^2$=H, $R^3$=$CHPh_2$, $R^4$=Ph, n=2, $R^5$=$CH_3$). The residue was purified by silica gel chromatography (benzene/ethyl acetate=1/1), giving 10.5 g (yield 70%) of compound (3b-2).

(Step B)

A 1.0 g quantity of compound (3b-2) ($R^1$=$PhCH_2CONH$, $R^2$=H, $R^1$=$CHPh_2$, $R^4$=Ph, n=2, $R^5$=$CH_3$) was dissolved in 10 ml of dimethylformamide dried with a molecular sieve 4 Å, and 1.6 g of weakly basic anion exchange resin (XE-583) was placed into the solution at 25° C. Disappearance of compound (3b-2) was confirmed by liquid chromatography 5 hours later, 100 ml of ethyl acetate was thereafter added to the reaction mixture, and the ethyl acetate layer was washed with water once, with aq. 1 N HCl once, with aq. 10% $NaHCO_3$ once and with 10% aqueous NaCl solution once. The ethyl acetate layer was dried over magnesium sulfate, followed by the removal of the solvent in vacuo to obtain a residue containing compound (4b) ($R^1$=$PhCH_2CONH$, $R^2$=H, $R^3$=$CHPh_2$, $R^4$=Ph, n=2. The residue was purified by silica gel chromatography (benzene/ethyl acetate=4/1 to 1/1), giving 0.82 g (yield 94%) of compound (4b).

EXAMPLES 4 TO 14

The reaction was conducted using compound (3a-1) in the same manner as in Example 1 except that the following basic anion exchange resin was used.

| Example | basic ion exchange resin | yield (%) |
|---------|--------------------------|-----------|
| 4 | IRA-35 | 94 |
| 5 | IRA-60E | 95 |
| 6 | IRA-93ZU | 90 |
| 7 | IRA-94 | 95 |
| 8 | IRA-94S | 96 |
| 9 | XT-6050 | 96 |
| 10 | WA-10 | 90 |
| 11 | WA-20 | 89 |
| 12 | WA-30 | 90 |
| 13 | DOWEX 66 | 92 |
| 14 | purolite A-103 | 91 |

EXAMPLE 15

[Allenization Reaction with Tertiary Organic Base, and Subsequent Treatment with Two Ion Exchange Resins, i.e., Acid Ion Exchange Resin and Basic Ion Exchange Resin]

(Step B)

A 1.0 g quantity of compound (3a-1) ($R^1$=$PhCH_2CONH$, $R^2$=H, $R^3$=p-$MeOC_6H_4CH_2$, $R^4$=Ph, n=2, $R^5$=$C_6H_4CH_3$) was dissolved in 10 ml of dimethylformamide dried with a molecular sieve 4 Å, and 0.45 ml of triethylamine was added dropwise to the solution at −20° C. over a period of 5 minutes. Disappearance of compound (3a-1) was confirmed by liquid chromatography 2 hours later, and 1.5 g of strongly acidic ion exchange resin (A-15E) was thereafter added to the reaction mixture at −20° C. One hour later, disappearance of the triethylamine as confirmed by gas chromatography, whereupon 1.5 g of weakly basic ion exchange resin (XE-583) was added to the reaction mixture, followed by stirring at 25° C. for 2 hours. The resins were filtered off after the reaction mixture was found free from p-toluenesulfonic acid (or the triethylamine salt thereof) by liquid chromatography. Ethyl acetate (100 ml) was added to the resulting reaction mixture, and the ethyl acetate layer was washed with water once, with aq. 1 N HCl once, with aq. 10% $NaHCO_3$ once and with 10% aqueous NaCl solution once. The ethyl acetate layer was dried over magnesium sulfate, followed by the removal of the solvent in vacuo to obtain a residue containing compound (4a) ($R^1$=$PhCH_2CONH$, $R^2$=H, $R^3$=p-$MeOC_6H_4CH_2$, $R^4$=Ph, n=2). The residue was purified by silica gel chromatography (benzene/ethyl acetate =4/1 to 1/1), giving 0.70 g (yield 96%) of compound (4a).

EXAMPLE 16

The following experiment was conducted to check the improved stability achieved by the resins.

A 1.0 g quantity of compound (3a-1) ($R^1$=$PhCH_2CONH$, $R^2$=H, $R^3$=p-$MeOC_6H_4CH_2$, $R^4$=Ph, n=2, $R^5$=$C_6H_4CH_3$) was dissolved in 10 ml of dimethylformamide dried with a molecular sieve 4 Å, and 0.45 ml of triethylamine was added dropwise to the solution at −20° C. over a period of 5 minutes. After disappearance of compound (3a-1) was confirmed by liquid chromatography 2 hours later, the reaction mixture was divided into two portions. One of the mixture portions was treated in the same manner as in Example 1. More specifically, 0.8 g of strongly acidic ion exchange resin (A-15E) was added to the reaction mixture at −20° C. Disappearance of the triethylamine was confirmed by gas chromatography 1 hour later, whereupon 0.8 g of weakly basic ion exchange resin (XE-583) was added to the resulting reaction mixture, followed by stirring at 25° C. for 2 hours. After the mixture was found free from p-toluenesulfonic acid (or the triethylamine salt thereof), the resins were filtered off to obtain reaction mixture (A) for use in the following experiment.

The other reaction mixture portion, i.e., reaction mixture (B), was used as it was for the experiment.

Each of reaction mixtures (A) and (B) was allowed to stand at room temperature for 2 hours, 50 ml of ethyl acetate was added to the mixture, and the ethyl acetate layer was washed with water once; with aq. 1N HCl once, with aq. 10% $NaHCO_3$ once and with 10% aqueous NaCl solution once, followed by drying over magnesium sulfate and removal of the solvent in vacuo. The residues obtained were checked for the content of allene compound for comparison. Reaction mixture (A) gave 0.36 g (yield 99%) of compound (4a), whereas reaction mixture (B) afforded no allene compound.

EXAMPLE 17

(Step B)

A 1.0 g quantity of compound (3b-1) ($R^1$=PhCH$_2$CONH, $R^2$=H, $R^3$=CHPh$_2$, $R^4$=Ph, n=2, $R^5$=C$_6$H$_4$CH$_3$) was dissolved in 10 ml of dimethylformamide dried with a molecular sieve 4 Å, and 0.45 ml of triethylamine was added dropwise to the solution at −20° C. over a period of 5 minutes. Disappearance of compound (3b-1) was confirmed by liquid chromatography 2 hours later, and 1.5 g of strongly acidic ion exchange resin (A-15E) was thereafter added to the reaction mixture at −20° C. One hour later, disappearance of the triethylamine was confirmed by gas chromatography, whereupon 1.5 g of weakly basic ion exchange resin (XE-583) was added to the reaction mixture, followed by stirring at 25° C. for 2 hours. The resins were filtered off after the reaction mixture was found free from p-toluenesulfonic acid (or the triethylamine salt thereof) by liquid chromatography. Ethyl acetate (100 ml) was added to the resulting reaction mixture, and the ethyl acetate layer was washed with water once, with 1 N HCl aq. once, with 10% $NaHCO_3$ aq. once and with 10% aqueous solution of NaCl once. The ethyl acetate layer was dried over magnesium sulfate, followed by the removal of the solvent in vacuo to obtain a residue containing compound (4b) 4$R^1$=PhCH$_2$CONH, $R^2$=H; $R^3$=CHPh$_2$, $R^4$=Ph, n=2). The residue was purified by silica gel chromatography (benzene/ethyl acetate =4/1 to 1/1),.giving 0.69 g (yield 93%) of compound (4b).

EXAMPLE 18

(Step B)

A 1.0 g quantity of compound (3b-2) ($R^1$=PhCH$_2$CONH, $R^2$=H, $R^3$=CHPh$_2$, $R^4$=Ph, n=2, $R^5$=CH$_3$) was dissolved in 10 ml of dimethylformamide dried with a molecular sieve 4 Å, and 0.45 ml of triethylamine was added dropwise to the solution at −20° C. over a period of 5 minutes. Disappearance of compound (3b-2) was confirmed by liquid chromatography 2 hours later, and 1.5 g of strongly acidic ion exchange resin (A-15E) was thereafter added to the reaction mixture at −20° C. One hour later, disappearance of the triethylamine was confirmed by gas chromatography, whereupon 1.5 g of weakly basic ion exchange resin (XE-583) was added to the reaction mixture, followed by stirring at 25° C. for 2 hours. The resins were filtered off after the reaction mixture was found free from methanesulfonic acid (or the triethylamine salt thereof) by liquid chromatography. Ethyl acetate (100 ml) was added to the resulting reaction mixture, and the ethyl acetate layer was washed with water once, with aq. 1 N HCl once, with aq. 10% $NaHCO_3$ once and with 10% aqueous NaCl solution once. The ethyl acetate layer was dried over magnesium sulfate, followed by the removal of the solvent in vacuo to obtain a residue containing compound (4b) ($R^1$=PhCH$_2$CONH, $R^2$=H, $R^3$=CHPh$_2$, $R^4$=Ph, n=2). The residue was purified by silica gel chromatography (benzene/ethyl acetate =4/1 to 1/1), giving 0.83 g (yield 95% ) of compound (4b)

EXAMPLES 19 TO 23

The reaction was conducted using compound (3a-1) in the same manner as in Example 15 except that the following acidic cation exchange resin and basic anion exchange resin were used.

| Example | acidic ion exchange resin | basic ion exchange resin | yield (%) |
|---------|---------------------------|--------------------------|-----------|
| 19 | A-15E | IRA-60E | 97 |
| 20 | A-15E | IPA-94S | 98 |
| 21 | A-15E | XT-6050 | 96 |
| 22 | A-15E | WA-10 | 90 |
| 23 | A-15E | DOWEX 66 | 96 |

REFERENCE EXAMPLE 1

The alllenyl β-lactam (4b) obtained according to the invention was converted to 3-chlorocephem (6) by the process disclosed in JP-A-282387/1992. The compound (6) was deprotected at the 7-position using phosphorus pentachloride an pyridine (JP-A-3356/1986) for conversion to compound (7), and an amide side chain was then introduced into the compound at the 7-position. Deprotection at the 4-position ester site afforded cefaclor (JP-A-39313/1986). The reaction formula is given below.

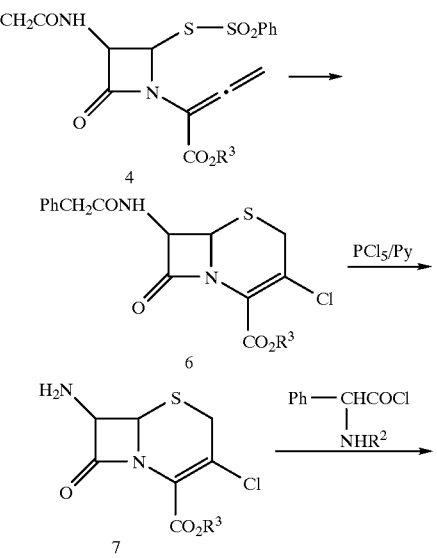

EXAMPLE 29

A 160 mg quantity of compound (4a) ($R^1$=PhCH$_2$CONH, $R^2$=H, $R^3$=CH$_2$C$_6$H$_4$OCH$_3$-p, $R^4$=Ph, n=2), 220 mg of aluminum chloride and 120 mg of lithium chloride were weighed out and placed into a 10-ml egg plant-type flask. With addition of 2 ml of N-methylpyrrolidone, the mixture was stirred at room temperature for 2 hours. The reaction mixture was poured into 1 N HCl and extracted with ethyl acetate, and the extract was washed with water twice and with brine once, and thereafter dried over anhydrous sodium sulfate. The resulting extract was concentrated in vacuo to remove the solvent and obtain a residue, which was thereafter purified by silica gel column chromatography, giving compound (6a, 119 mg, 91%)
$^1$H NMR (CDCl$_3$) δ:3.42(d, J =17.8 Hz, 1H), 3.72(d, J=17.8 Hz, 1H), 3.58(d, J=16.4 Hz, 1H), 3.64(d, J=16.4 Hz, 1H), 3.79(s, 3H), 4.96(d, J=5.1 Hz, 1H), 5.21(s, 2H), 5.79(dd, J=5.1, 9.2 Hz, 1H), 6.39(d, J=9.2 Hz, 1H), 6.82–7.40(m, 9H)

EXAMPLE 30

The reaction was conducted in the same manner as in Example 1except that Compound (4b)($R^1$=$^{PhCH}$$_2$CONH, $R^2$=H, $R^3$=CHPh$_2$, $R^4$=Ph, n=2) was used as a starting material to obtain Compound 6b (123 mg, 93% ).
$^1$H NMR (CDCl$_3$) δ:3.43(d, J=18.9 Hz, 1H), 3.58(d, J=16.2 Hz, 1H), 3.65(d, J=16.2 Hz, 1H), 3.73(d, J=18.9 Hz, 1H), 4.99(d, J=4.8 Hz, 1H), 5.83(dd, J=4.8, 9.3 Hz, 1H), 6.24(d, J=9.3 Hz, 1H), 6.97(s,1H), 7.21–7.42(m, 15H)

EXAMPLES 31 TO 36

The reaction was conducted using compound (4a) as a starting material in the same manner as in Example 29 except that the following sulfinate ion or thiolate ion capturing agent was used.

| Example | capturing agent | yield (%) |
|---|---|---|
| 31 | aluminum bromide | 85 |
| 32 | aluminum iodide | 82 |
| 33 | O,N-bistrimethylsilylacetamide | 90 |
| 34 | bistrimethylsilylurea | 89 |
| 35 | hexamethyidisilane | 85 |
| 36 | trimethyisilylchloride | 82 |

EXAMPLES 37 TO 49

The reaction was conducted using compound (4a) as a starting material in the same manner as in Example 29 except that acid halide, acid anhydride, sulfonyl halide or sulfonic andydride was used as the sulfinate ion or thiolate ion capturing agent.

| Example | capturing agent | yield (%) |
|---|---|---|
| 37 | acetyl chloride | 89 |
| 38 | trifluoroacetyl chloride | 82 |
| 39 | acetoxyacetyl chloride | 79 |
| 40 | chloroacetyl chloride | 80 |
| 41 | acetoacetyl chloride | 76 |
| 42 | acetic anhydride | 86 |
| 43 | trifluoroacetic anhydride | 88 |
| 44 | methanesulfonyl chloride | 80 |
| 45 | benzenesulfonyl chloride | 83 |
| 46 | toluenesulfonyl chloride | 79 |
| 47 | methanesulfonic anhydride | 78 |
| 48 | trifluoromethanesulfonic anhydride | 87 |
| 49 | toluenesulfonic anhydride | 78 |

EXAMPLES 50 TO 59

The reaction was conducted using compound (4a) as a starting material in the same manner as in Example 29 except that the following halogenating agent was used.

| Example | halogenating agent | yield (%) |
|---|---|---|
| 50 | AlCl$_3$ | 90 |
| 51 | TiCl$_4$ | 85 |
| 52 | SnCl$_2$ | 80 |
| 53 | SnCl$_4$ | 82 |
| 54 | ZnCl$_2$ | 81 |
| 55 | CaCl$_2$ | 87 |
| 56 | SrCl$_2$ | 86 |
| 57 | NaCl | 80 |
| 58 | KCl | 78 |
| 59 | MgCl$_2$ | 75 |

EXAMPLES 60 TO 64

The reaction was conducted using compound (4a) as a starting material in the same manner as in Example 29 except that the following solvent was used.

| Example | solvent | yield (%) |
|---|---|---|
| 60 | DMF | 90 |
| 61 | DMSO | 85 |
| 62 | HMPA | 70 |
| 63 | DMA | 83 |
| 64 | THF | 86 |

REFERENCE EXAMPLE 2

Compound (6b) obtained by the present invention can be converted to cefaclor which is widely used in the form of oral preparations, by processes disclosed in literature. More specifically, compound (6) is deprotected at the 7-position using phosphorus pentachloride and pyridine (JP-A-3356/1986) and converted to compound (7), into which an amide side chain is thereafter introduced at the 7-position. Cefaclor can be obtained when the compound is subsequently deprotected at the 7-position ester site (JP-A-39313/1986). The reaction formula is given below.

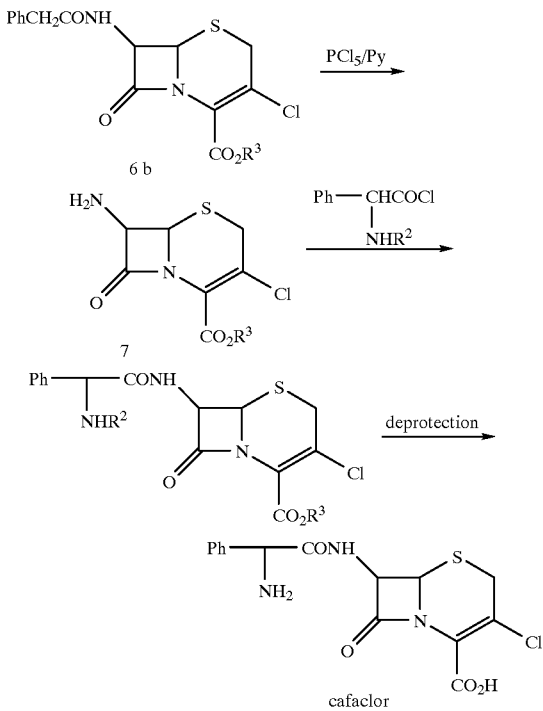

cafaclor

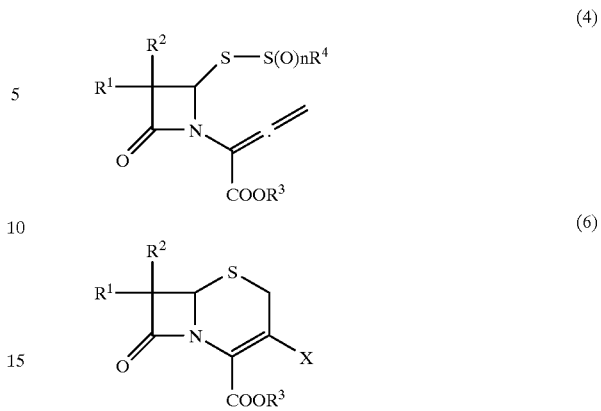

(INDUSTRIAL APPLICABILITY)

The invention provides an allenyl β-lactam compound (4) with stability and high purity in high yield which compound can be readily converted to 3-chlorocephalosporin, a useful intermediate for preparing, for example, cefaclor commercially available for oral administration.

Furthermore, a 3-halogenated cephem derivative of the formula (6) is prepared with a high purity and in a high yield through a safe and simplified procedure, by causing a halogenating agent to act on the allenyl β-lactam compound of the formula (4) in the presence of an agent for capturing sulfinate ion or thiolate ion.

We claim:

1. A process for preparing a 3-halogenated cephem derivative represented by the formula (6), characterized by causing a halogenating reagent to act on an allenyl β-lactam compound represented by the formula (4) in the presence of a sulfinate ion or thiolate ion capturing agent selected from the group consisting of trimethylsilyl halide, 0, N-bistrimethylsilylacetamide, bistrimethylsilylurea, hexamethyldisilazane, hexamethylsilylacetamide, lower alkyl acid halide, lower alkyl carbonic acid halide, diacid halide, lower alkyl acid anhydride, sulfonyl halide, sulfonic anhydride and aluminum halide, wherein said diacid halide is at least one of oxalyl chloride, tartaryl dichloride, succinyl dichloride and malonyl dichloride and said sulfonyl halide is selected from the group consisting of lower alkylsulfonyl chloride, arylsulfonyl chloride and halogenosulfonyl chloride, to obtain the 3-halogenated cephem derivative wherein $R^1$ is a hydrogen atom, amino or protected amino, $R^2$ is a hydrogen atom, halogen atom, lower alkoxyl formyl, acetyl, propionyl, butyryl, isobutyryl, or lower alkyl having hydroxyl or protected hydroxyl as a substituent, $R^3$ is a hydrogen atom or carboxylic acid protecting group, $R^4$ is an aromatic group which may have a substituent, or nitrogen-containing aromatic heterocyclic group which may have a substituent, wherein said substituent is selected from the group consisting of halogen atoms, straight-chain or branched $C_{1-4}$ alkoxyl group, straight-chain or branched $C_{1-4}$ alkylthio groups, straight-chain or branched $C_{1-4}$ alkylsulfonyloxy groups, aromatic sulfonyloxy or methyl-substituted aromatic sulfonyloxy, straight-chain or branched $C_{1-4}$ alkyl groups, amino, amino which has as a substituent one or two straight-chain or branched $C_{1-4}$ alkyl groups, hydroxyl, acyloxy group represented by R'COO— wherein R' is phenyl, tolyl, or straight-chain or branched $C_{1-4}$ alkyl group, acyl group represented by R'CO— wherein R' is as defined above, nitro, cyano, and phenyl, and n is 0 to 2, X is a halogen atom.

2. A process as defined in claim 1 wherein the acid halide is lower alkyl acid halide or bivalent acid halide selected from the group consisting of oxalyl chloride, tartaryl dichloride, succinyl dichloride, and malonyl dichloride.

3. A process as defined in claim 1 wherein the acid anhydride is lower alkyl acid anhydride selected from the group consisting of acetic anhydride, trifluoroacetic anhydride, succinic anhydride and malonic anhydride.

4. A process as defined in claim 1 wherein the sulfonic anhydride is lower alkylsulfonic anhydride, arylsulfonic anhydride or halogenosulfonic anhydride.

5. A process as defined in claim 1 wherein the halogenating reagent is aluminum halide, silyl halide, halogen salt of alkali metal and alkaline earth metal or a quaternary ammonium halide selected from the group consisting of ammonium chloride, triethylamine hydrochloride, tetra-n-butylammonium chloride, triethylbenzylammonium bromide and tetrabenzylammonium halide.

6. A process as defined in claim 1 wherein the aromatic sulfonyloxy is toluenesulfonyloxy.

7. A process as defined in claim 5 wherein the silyl halide is trimethylsilyl halide.

8. A process as defined in claim 1 wherein a silyl halide or aluminum halide is both the sulfinate ion or thiolate ion capturing agent and the halogenating reagent.

9. A process as defined in claim 8 wherein the silyl halide is trimethylsilyl halide.

* * * * *